(12) United States Patent
Eid

(10) Patent No.: US 7,066,878 B2
(45) Date of Patent: Jun. 27, 2006

(54) PENILE PROSTHESIS AND SURGICAL INSTRUMENTS FOR IMPLANTATION OF PENILE PROSTHESES

(75) Inventor: J. Francois Eid, Larchmont, NY (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

(21) Appl. No.: 10/713,437

(22) Filed: Nov. 14, 2003

(65) Prior Publication Data

US 2004/0225182 A1    Nov. 11, 2004

Related U.S. Application Data

(60) Provisional application No. 60/426,217, filed on Nov. 14, 2002.

(51) Int. Cl.
*A61F 5/00* (2006.01)
(52) U.S. Cl. ....................................................... 600/40
(58) Field of Classification Search ............ 600/38–41; 606/40, 108, 119, 126, 139, 148, 190; 623/66.1, 623/902, 909, 661
See application file for complete search history.

(56) References Cited

U.S. PATENT DOCUMENTS

| | | | |
|---|---|---|---|
| 3,929,138 A * | 12/1975 | Curi ............................ 606/167 |
| 4,244,370 A | 1/1981 | Furlow et al. |
| 4,424,807 A | 1/1984 | Evans, Sr. |
| 4,651,721 A | 3/1987 | Mikulich et al. |
| 4,653,485 A | 3/1987 | Fishell |
| 4,726,360 A | 2/1988 | Trick et al. |
| 4,959,067 A * | 9/1990 | Muller ........................ 606/190 |
| 4,964,417 A * | 10/1990 | Peters ......................... 128/850 |
| 5,062,417 A | 11/1991 | Cowen |
| 5,088,477 A | 2/1992 | Subrini |
| 5,109,869 A * | 5/1992 | Buckley ...................... 600/591 |
| 5,234,438 A * | 8/1993 | Semrad ....................... 606/108 |
| 5,263,981 A | 11/1993 | Polyak et al. |
| 5,382,256 A | 1/1995 | Del Castillo |
| 5,397,330 A * | 3/1995 | Mikhail ....................... 606/88 |
| 5,484,450 A | 1/1996 | Mohamed |
| 5,643,288 A * | 7/1997 | Thompson ................... 606/139 |
| 5,749,877 A * | 5/1998 | Young .......................... 606/99 |
| 5,824,010 A | 10/1998 | McDonald |
| 5,868,729 A * | 2/1999 | Pelfrey ......................... 606/1 |
| 6,319,272 B1 * | 11/2001 | Brenneman et al. ......... 606/232 |

FOREIGN PATENT DOCUMENTS

WO    WO 03/071970 A1    9/2003

OTHER PUBLICATIONS

The Erectile Dysfunction Guide- AMS Penile Prosthesies Product Line Jul. 1, 2002.
Penile Prosthesis Implantaion E-Medicine, Oct. 15, 2003 Yao-Jen Chang, MD.

* cited by examiner

*Primary Examiner*—Samuel G. Gilbert
(74) *Attorney, Agent, or Firm*—Kimberly K. Baxter

(57) ABSTRACT

The invention relates to an improved penile erection device and improved method for implanting such devices into the corpus cavernosum of the penis. The invention further relates to tools for implanting the improved penile erection device. Furthermore, the invention relates to insertion tools that permit precise placement of conventional inflatable prostheses cylinders such that puncture or damage of the glans penis does not occur during placement.

14 Claims, 9 Drawing Sheets

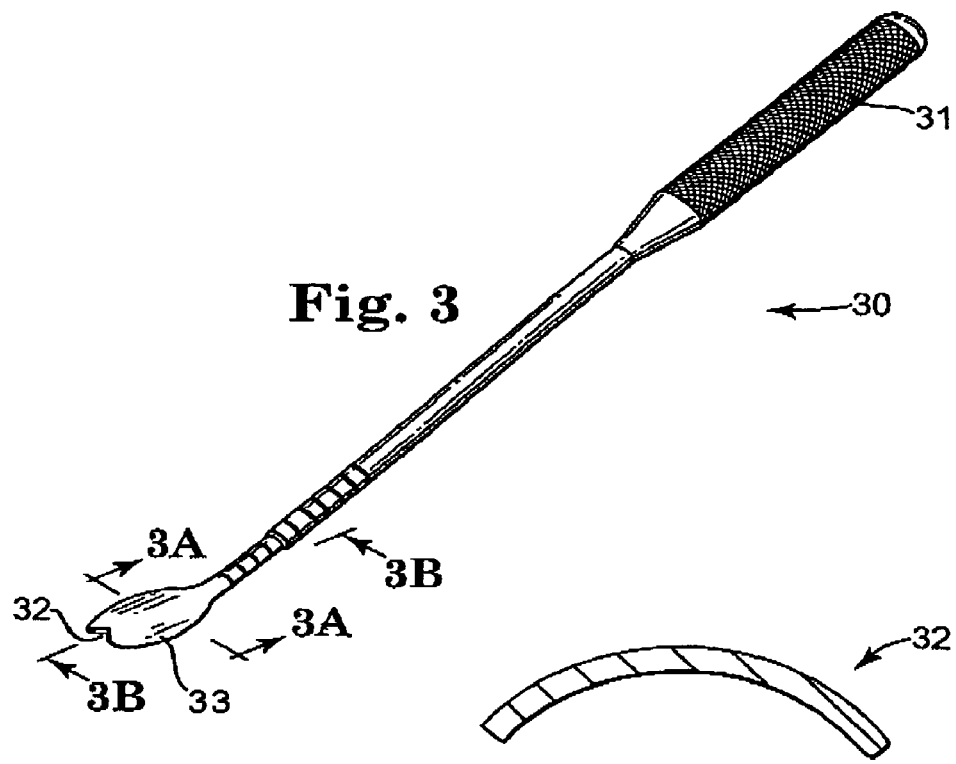
Fig. 3
Fig. 3A
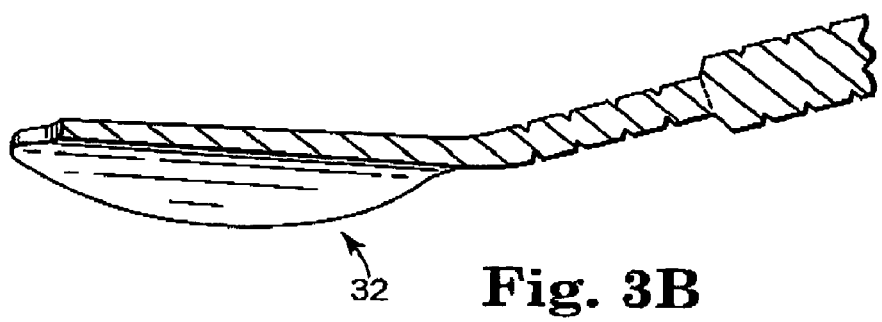
Fig. 3B

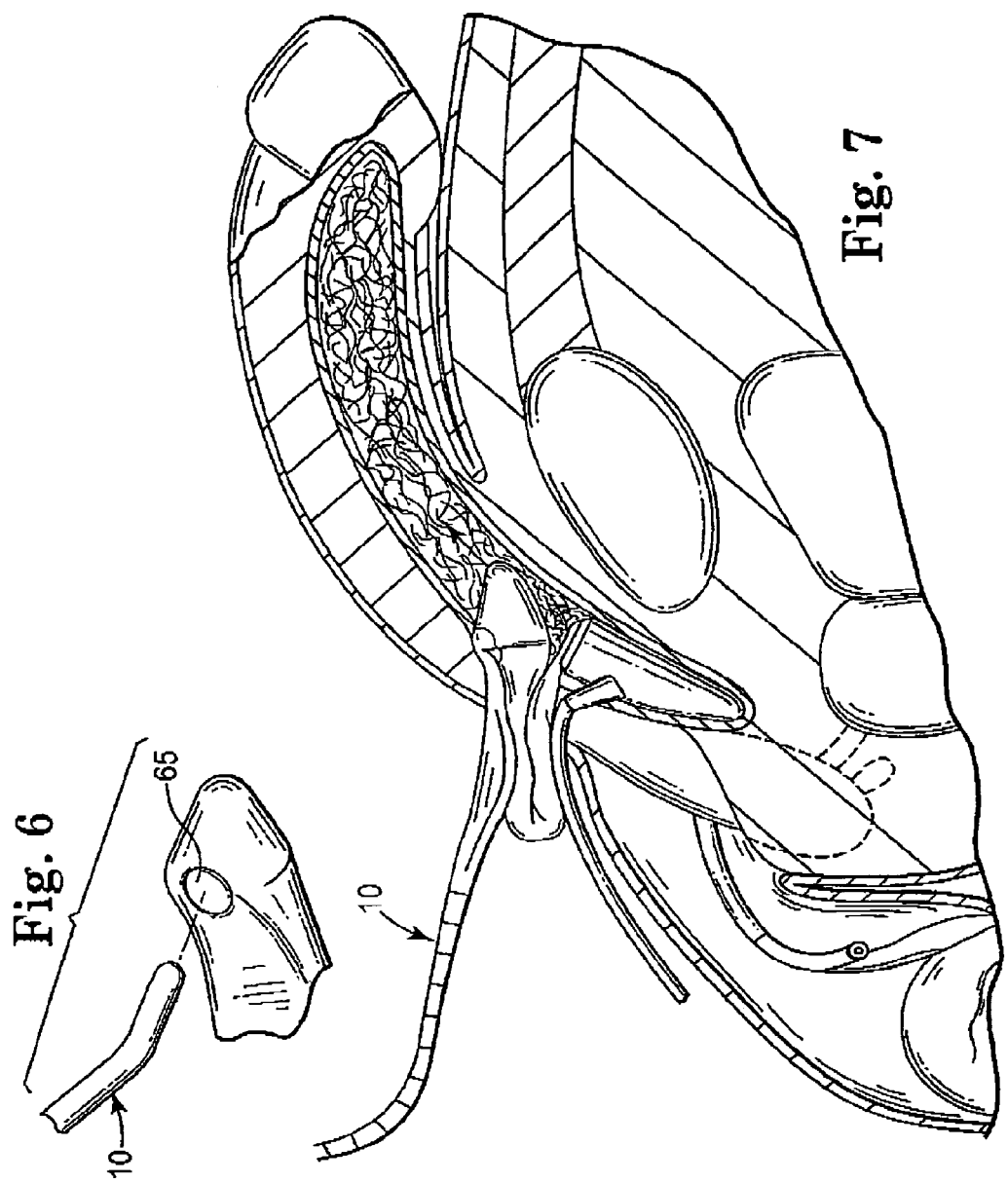

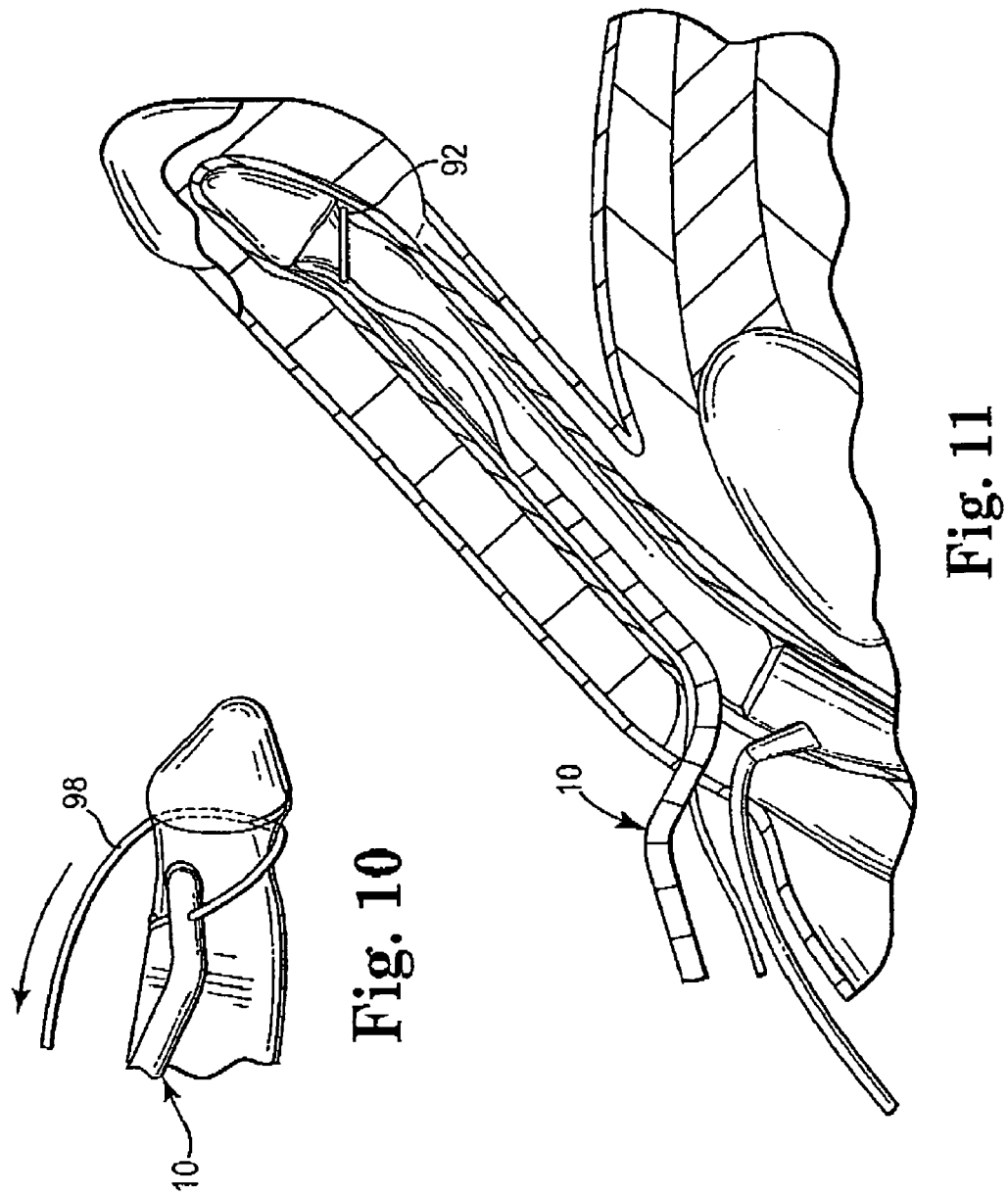

PENILE PROSTHESIS AND SURGICAL INSTRUMENTS FOR IMPLANTATION OF PENILE PROSTHESES

This application claims the benefit prov. appln. No. 60/426,217, filed on Nov. 14, 2002.

FIELD OF THE INVENTION

The invention relates generally to the field of penile erection devices and instruments for penile prosthesis implantation. More particularly, the invention relates to an improved penile erection device and improved method for implanting such devices into the corpus cavernosum of the penis. The invention further relates to insertion tools that permit precise placement of conventional inflatable prostheses cylinders such that puncture or damage of the glans penis does not occur during placement.

BACKGROUND OF THE INVENTION

Various types of implantable penile prostheses are available for treatment of erectile dysfunction, and various specialized tools exist for implanting such prostheses. A typical penile prosthesis includes at least one pair of cylinders that are inflatable and are each implantable in one of the corpus cavernosa. The penile prosthesis further includes a pump external to the cylinder for pressurizing the cylinder. The pump is typically connected to the cylinder through a tubing near the proximal end of the cylinder. Each cylinder has a fluid tube connected thereto between the ends at a position spaced further from the distal end and closer to the proximal end thereof. A pump is disposed in the scrotum, and connected through tubing to a spherical abdominal reservoir. The reservoir is placed in the pelvic area near the urinary bladder behind the muscles of the abdominal wall. The cylinders are inflated as fluid is pumped from the reservoir, and are deflated as fluid is transferred back to the reservoir. This inflation and deflation allows the patient to control whether his penis is erect or flaccid. An example of such penile prosthesis is the AMS 700™ inflatable penile prosthesis manufactured by American Medical Systems, Inc. Further illustrative of the devices available is that disclosed in U.S. Pat. No. 4,590,927 that relates to a unitary penile prosthesis which comprises a tubular enclosure having a distal portion which includes a pump, a medial portion including a pressurizable chamber which contains an internal tubular, substantially non-distensible portion and a concentric tubular sleeve, and a proximal portion defining a fluid reservoir therewithin.

Both U.S. Pat. No. 4,350,151 and U.S. Pat. No. 4,244,370 disclose tools, respectively known as the Scott and Furlow et al. tools, which among other things are used to introduce a suture-carrying needle into the penile corporus cavernosa. Thus, example of surgical procedures employed in the art to implant penile prostheses provide that a tool known as the "Furlow Introducer" shoots a long straight needle (the "Keith Needle") which holds a traction suture to a distal tip of the penile prosthesis cylinder. The Keith Needle is pushed with the Furlow Introducer through the glans penis in order to position the distal tip of the prosthesis underneath the proximal aspect of the glans penis. This approach is not entirely satisfactory because it does not permit placement of the prosthesis cylinder in the penis without puncturing of the glans penis and resulting in bleeding.

Similar and greater difficulties are encountered in the art with respect to positioning of the proximal tip of prosthesis cylinder in the penis. Difficulties are presented with respect to placement of the proximal tip without current instruments slipping off the cylinder, measurement of the placement of the proximal tip of the cylinder in the corpora of the penis, and reconciling this measurement with the total measurement of the penile length. It has also been difficult to achieve this placement without damaging the prosthesis Instruments have been developed to assist in closing an incision made for the purpose of implanting the prosthesis. An example of such an instrument is disclosed in U.S. Pat. No. 5,484,450. The instrument comprises a very short arcuate spoon-like element welded on its convex side to a rigid, rod-shaped element. The distal end of the rod-shaped element has a V-shaped notch formed in the exterior thereof. The notch enables a suture needle to extend therethrough during a suturing operation to close the incision. The instrument has been found difficult to use since it is difficult to coordinate or align the V-shaped notch with the suture needle during the incision closing procedure.

Thus, there is a need in the art for an improved penile prosthesis that can be implanted without the use of needles, which can puncture the glans penis and the penile prosthesis, and instruments useful for implanting such improved penile prosthesis.

There is a further need for instruments useful in implanting the distal end of existing conventional penile prostheses without the use of needles and the possibility of puncturing the penile prosthesis and the glans penis. There also exists a need to provide an implant incision-closing instrument, which is more convenient to use and otherwise overcomes the disadvantages of the instruments of the prior art. There are no widely used tools specifically designed to assist in the implantation of the proximal cylinder end of penile prosthesis. Thus, there is a continuing need for penile implantation tools of this type that are safe, easy to use and versatile.

The invention disclosed herein is aimed at providing tools that achieve one or more of these goals while having substantially fewer drawbacks of the conventional tools. The invention is further aimed at providing an improved penile erection device and improved method for implanting such devices into the corpus cavernosum of the penis.

SUMMARY OF THE INVENTION

The present invention overcomes the problems associated with previous devices and implantation methods by providing improved penile prostheses that do not require the use of needles for implantation. The present invention further provides implantation tools for implanting such improved penile prostheses.

The present invention further overcomes the problems associated with previous implantation methods by providing implantation tools for implanting conventional penile prostheses.

Thus, an object of the present invention is to provide an improve penile prosthesis that is essentially characterized in that the cylinder has a cradle at the distal segment which enables the cylinder to be inserted into the corpus carvernosum without the use of a traction suture and needle which can puncture the glans penis.

Another object of the present invention is to provide an improved penile prosthesis that is essentially characterized in that the cylinder has a cradle at the distal segment which enables the cylinder to be inserted into the corpus carvernosum without the use of a traction suture and needle which can puncture the glans penis, wherein the cradle is made by a cap or fold that is attached to the tip of the cylinder, said cap or fold made of a softer silicone thereby enabling the fold to open when the tool is inserted and fold back or close when the tool is removed.

An object of the present invention is to provide a penile prosthesis that is generally in the form of an elongate body made from synthetic material, of a thickness generally equal to or greater than 10 to 13 mm, and the cradle is located about 5 mm from the distal tip of the cylinder.

Another object of the present invention is to provide a penile prosthesis that is of any appropriate material tolerated by the tissues, and in particular silicone.

Another object of the present invention is to provide a method of implanting the distal tip of the improved penile prosthesis of the present invention wherein the cylinder is totally deflated prior to insertion into the corpus carvernosum, thus allowing the surgeon to insert the entire cylinder through a small aperture without requiring large incision of the corpora.

Another object of the present invention is to provide a method of implanting the distal tip of the improved penile prosthesis of the present invention wherein the cylinder is totally deflated prior to insertion into the corpus carvernosum, thus allowing the surgeon to insert the entire cylinder through a small aperture without requiring large incision of the corpora, wherein the penile prosthesis is a multi-component inflatable penile prosthesis.

Another object of the present invention is to provide a method of implanting the distal tip of the improved penile prosthesis of the present invention said method comprising the steps of inserting a completely deflated cylinder into the corpus carvernosum, positioning the prosthesis at the distal tip, securing the distal tip by holding the tip of the glans penis, disengaging the tool from the cradle, and pulling the tool back out of the glans penis.

Another object of the present invention is to provide a method of implanting the improved penile prosthesis of the present invention wherein bleeding and infection may be prevented.

Another object of the present invention is to provide a method of implanting the improved penile prosthesis of the present invention wherein post-operative scarring is decreased.

Another object of the present invention is to provide a method of implanting the improved penile prosthesis of the present invention wherein the costs of implanting the penile prosthesis is reduced.

A further object of the present invention is to provide an instrument for precise surgical implantation of the improved penile prostheses characterized in that the tip of the tool is designed so that it fits into the cradle located on the tip of the cylinder.

A further object of the present invention is to provide an instrument for precise surgical implantation of the improved penile prostheses characterized in that the tip of the tool is designed so that it fits into the cradle located on the tip of the cylinder, wherein said tool comprises an elongated shaft including a handle at one end and a blunt end at the opposite end, and wherein said blunt end is designed to conform to the cradle in the prosthesis.

A further object of the present invention is to provide an instrument for precise surgical implantation of the improved penile prostheses without puncturing the glans penis or the penile prosthesis.

Another object of the present invention is to provide a tool for surgical placement of the proximal tip of the penile prosthesis, which tool comprises an elongate shaft including a handle at one end and at an opposing end a receptacle which conforms to and supports the junction of the prosthesis cylinder and the connection with the tubing of the prosthesis.

Another object of the present invention is to provide a tool for surgical placement of the proximal tip of the penile prosthesis, wherein the receptacle has a convex cross-section and fusiform configuration.

Another object of the present invention is to provide a tool for surgical placement of the proximal tip of the penile prosthesis, wherein the receptacle has a smooth peripheral edge and finish which guards against damage to the penile tissue and the penile prosthesis device in the surgical placement of the prosthesis.

Another object of the present invention is to provide a tool for surgical placement of the proximal tip of the penile prosthesis, wherein the receptacle does not have sharp edges which prevents entanglement with the sutures during corporotomy closure.

Another object of the present invention is to provide a tool for surgical placement of the proximal tip of the penile prosthesis, wherein the outer surface of the handle is etched with numbers and grooves to permit precise positioning of the prosthesis in the penis.

Another object of the present invention is to provide a tool for surgical placement of the proximal tip of the penile prosthesis which guards against damage to penile tissue and the prosthesis device in the surgical placement of the prosthesis.

An object of the present invention is to provide a tool for surgical placement of the distal tip of existing conventional penile prostheses without requiring the use of needles, which can puncture the glans penis and the penile prosthesis.

An object of the present invention is to provide a tool for surgical placement of the distal tip of existing conventional penile prostheses which tool comprises an elongate shaft including a handle at one end, and an opening for receiving a suture at the opposite end.

An object of the present invention is to provide a tool for surgical placement of the distal tip of existing conventional penile prostheses wherein the handle of the tool has measurements, etchings calibrated to accommodate prosthesis dimensions and inform the operator of the exact distance of the distal tip inside the penile shaft to a reference point at the site of entry into the penile shaft.

An object of the present invention is to provide a tool for surgical placement of the distal tip of existing conventional penile prostheses which tool comprises an elongate shaft including a handle at one end, and an opening for receiving a suture at the opposite end, wherein the suture is secured around the shaft opening to secure the cylinder to the tool.

An object of the present invention is to provide a tool for surgical placement of the distal tip of existing conventional penile prostheses which tool comprises an elongate shaft including a handle at one end, and an opening for receiving a suture at the opposite end, wherein the suture is secured through a tunnel located on the tip of the distal prosthetic to fasten the cylinder to the tool.

A further object of the present invention is to provide a closing tool for surgical placement of the penile prosthesis.

A further object of the present invention is to provide a closing tool for surgical placement of the penile prosthesis, which protects the prosthesis cylinder from damage by a suturing needle.

A further object of the present invention is to provide a closing tool for surgical placement of the penile prosthesis, which includes a shaft with a grip or handle at one end and a protective shield member at its opposite end, wherein the shield overlies the glans penis and is employed to protect the prosthesis cylinder from damage by a suturing needle.

BRIEF DESCRIPTION OF THE FIGURES

FIG. 3 schematically illustrates another embodiment of the insertion tool for placement of the proximal tip of the penile prosthesis.

FIG. 3A schematically illustrates the receptacle portion of the insertion tool shown in FIG. 3.

FIG. 3B schematically illustrates the receptacle portion of the insertion tool shown in FIG. 3.

FIG. 6 illustrates the implantation of a deflated cylinder of the present invention containing a cradle on the distal tip of the cylinder, together with the insertion tool.

FIG. 7 illustrates the implantation of a cylinder containing a cradle on the distal tip of the cylinder together with the insertion tool.

FIG. 10 schematically illustrates insertion of the distal tip of the cylinder without the use of needles, wherein the suture is utilized to secure the distal tip.

FIG. 11 schematically illustrates insertion of the distal tip of the cylinder without the use of needles, wherein the suture is utilized to secure the distal tip.

Figure 1:
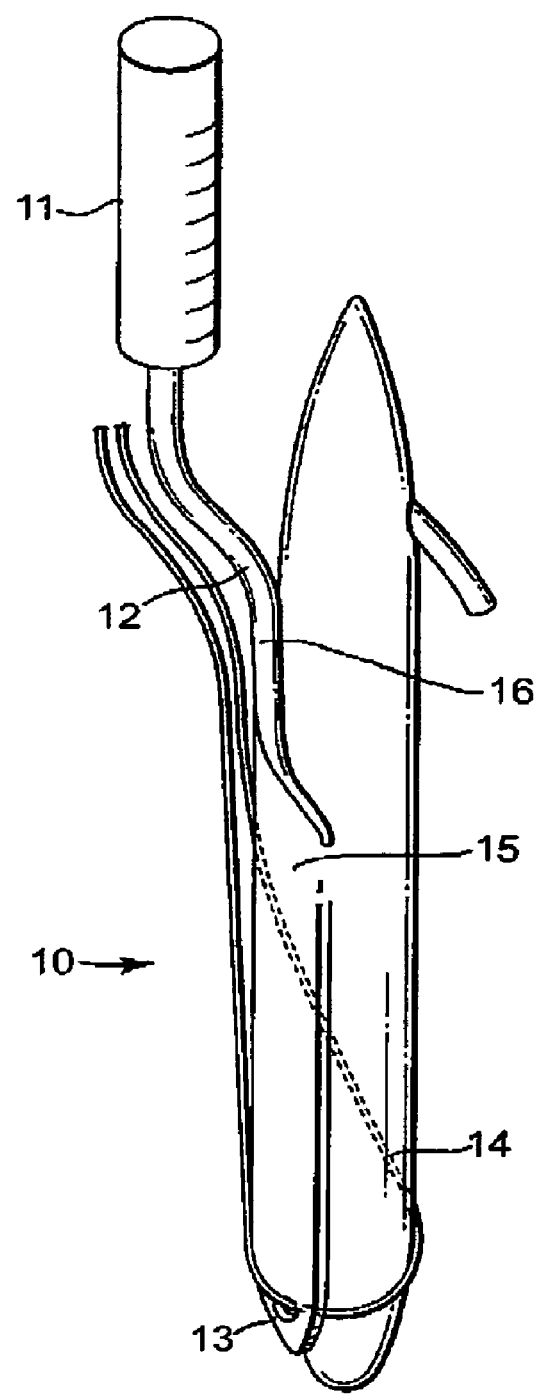
FIG. 1 schematically illustrates a penile implant prosthesis together with the insertion tool for placement of the distal tip of the penile prosthesis.

While the invention is susceptible to various modifications and alternative forms, specific embodiments thereof have been shown by way of example in the drawings and are herein described in detail. It should be understood, however, that the description herein of specific embodiments is not intended to limit the invention of the particular forms disclosed, but on the contrary, the invention is to cover all modifications, equivalents, and alternatives falling within the spirit and scope of the invention as defined by the appended claims.

DETAILED DESCRIPTION OF THE INVENTION

As used in the present application the term proximal is meant to convey the part of the body that is situated next to or near the point of attachment or origin or a central point: as located toward the center of the body. As used in the present application the term distal is meant to convey the part of the body that is situated away from the point of attachment or origin or a central point: as located away from the center of the body Distal Tip Insertion Tool Referring to FIG. 1, the insertion tool 10 in one embodiment of the invention has an elongate shaft and includes a substantially round handle portion 11, a thinner portion 12, and a distal tip portion 13. Intermediate the thinner portion 12 and the distal tip portion 13, the insertion tool 10 includes outwardly angled shaft section 15, and linear handle section 16 that is aligned in space and parallel relation to the axis of the shaft. The distal tip portion 13 preferably includes an opening for receiving a suture 14, thus eliminating the need for needles to drag the distal tip of the cylinder.

Referring to FIGS. 10 and 11, in practice, a suture is secured around the shaft opening to secure the cylinder to the tool. The suture may also be secured through a tunnel located on the tip of the distal prosthetic to fasten the cylinder to the tool. Advantageously, the tool permits the surgeon to precisely position the distal tip of the prosthesis cylinder for implantation. The handle of the tool has measurements, etchings calibrated to accommodate prosthesis dimensions and inform the operator of the exact distance of the distal tip inside the penile shaft to a reference point at the site of entry into the penile shaft.

The outwardly angled shaft section 15 preferably has a convexity and a width size ranging from about 0.5 cm to about 1.5 cm. The tool 10 has a hole in the tip, which is preferably about ⅛th of an inch from the distal tip. The insertion tool of FIG. 1 is designed fro the surgical placement of the distal tip of existing conventional penile prosthesis without puncturing the glans penis.

A typical conventional penile implant prosthetic device for the distal tip insertion tool of the invention is particularly useful, includes existing penile prosthesis having a cylinder or tubular enclosure, implantable in a corpus cavernosum, a pump bulb, to be disposed outside corpus cavernosum (typically implanted in the scrotum), and a tubing and the bulb. The cylinder includes a proximal portion a medial portion and a distal portion. The medial portion is flexible and can be pressurized by fluid pumped from the bulb via the tubing. The proximal portion is substantially more rigid than the medial portion and includes the junction between the cylinder and tubing. The cylinder further includes a distal portion which may have a tunnel located on the distal tip wherein the suture can be secured.

Proximal Tip Insertion Tool

Figure 2:
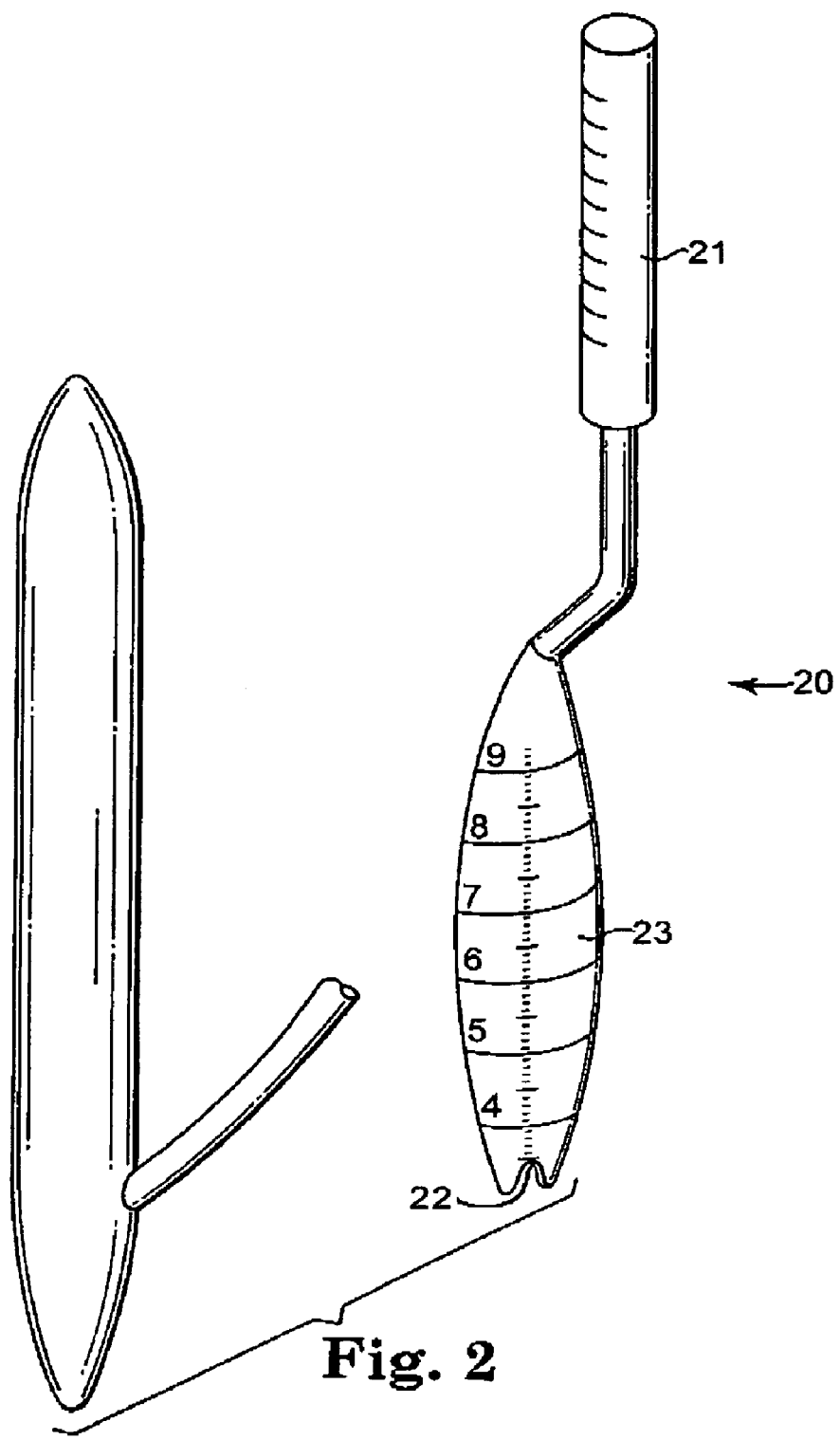
FIG. 2 schematically illustrates a penile implant prosthesis together with the insertion tool for placement of the proximal tip of the penile prosthesis.

Referring to FIGS. 2 and 3, the insertion tools 20 end 30, in one embodiment of the invention have an elongated shaft 23 and 33 including a handle 21 and 31 at one end and at an opposing end a receptacle 22 and 32 which conforms to and supports the junction of the prosthesis cylinder and connection with the tubing. A notch of similar diameter with the tubing is utilized as the receptacle. At its widest cross-section, the receptacle has a dimension of approximately one centimeter. The receptacle has a smooth peripheral edge and finish which guards against damage to penile tissue and the prosthesis device in the surgical placement of the prosthesis. The insertion tools 20 and 30 having the further advantage of not having sharp angles which get entangled with the sutures during corporotomy closure.

The other surface of the handle 21 and 31 is etched with numbers and grooves to permit precise positioning of the prosthesis in the penis. The etchings and measurements may be calibrated to accommodate prosthesis dimensions. For example, for use with an AMS brand penile prosthesis, tools 20 and 30 may be etched with numbers and grooves every millimeter starting at 3 cm (the tubing connects with the rear tip at 3 cm fro the rear tip) and ending at 10 cm.

With reference to FIGS. 2 and 3 the proximal rear tip of the penile prosthesis may be housed in the overlying relation to the receptacle with the distal tip of the prosthesis extending towards the handle. This permits the precisely placement of the prosthesis with reference to calibrations on the tool. The notch at the end of the receptacle prevents the tool from slipping off the prosthesis cylinder and the etched measurements on the rod-like element inform the operator of the exact location of the proximal tip in the crura of the penis vis a vis a fixed traction suture at the edge of the point of entrance in the penile shaft. It will be understood that the dimensions of the proximal tip insertion tools of the present invention will vary to accommodate like dimension of the prosthesis.

Referring to FIGS. 3A and 3B, the insertion tool 30 in one embodiment of the invention the receptacle has a convex cross-section and fusiform configuration.

The Closing Tool

Figure 4:
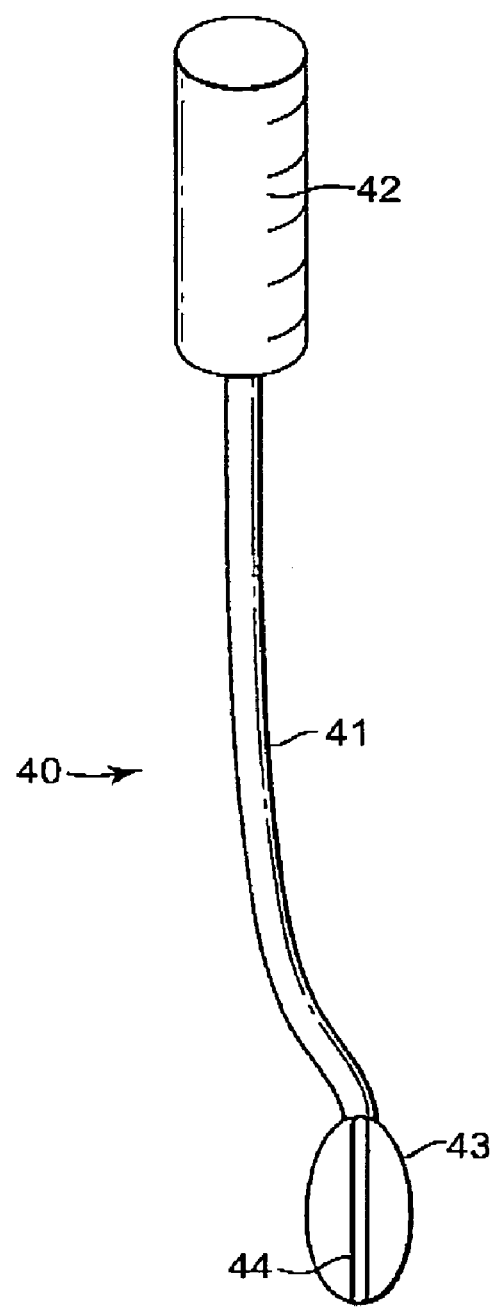
FIG. 4 schematically illustrates the closing tool.

Referring to FIG. 4, the closing tool 40 in one embodiment of the invention includes a shaft 41 with a grip or handle 42 at one end and a protective shield member at its opposite end 43. The shield overlies the penis and is employed to protect the prosthesis cylinder from damage by a suturing needle. In general, known closing tools are not entirely satisfactory in that they are characterized by use of sharp edges, short (narrow leafs) spoon like element with acute angles welded to the end of a rod-shaped element. In practice, the prosthesis cylinders, which are fabricated of silicone elastomers, are damaged by the sharp edges of the closure tool. Further difficulties arise in use when the closing tool becomes snagged in the suture complicating removal of the closing tool from the corpora. Finally, leafs of the closing tool are narrow and short making it difficult to protect the prosthesis cylinder from the suture needle, without having to move and adjust the tool.

The improved closing tool of the present invention 40 permits closure of the corpora without damage to the cylinders of the prosthesis. The closing tool includes a handle 42 attached to a narrow shaft that at its base is angled outward from the axis of the shaft. A convex shaped shield with smooth contour and thick edges is positioned at the distal end of a rod-like element. According to the invention, the convex shield is dimensioned to conform to the configuration of the prosthesis, that is, the specific cylinder in use, and provided with smooth and rounded edges. This feature guards against snagging of the suture during closure of the corpora or other damage to the prosthesis.

Penile Prosthesis

Figure 5:
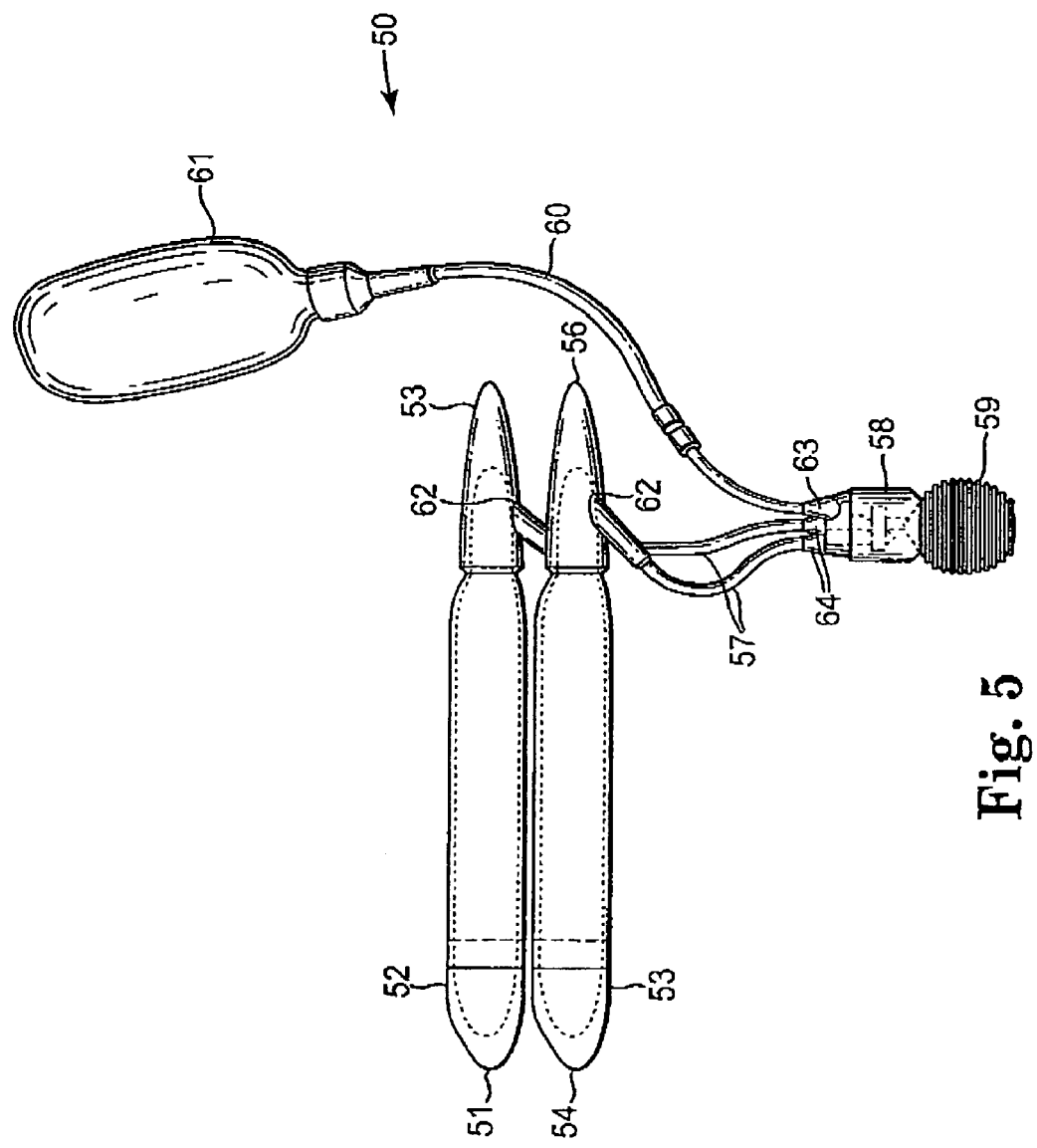
FIG. 5 schematically illustrates a penile implant prosthesis.

As shown in FIG. 5, the penile implant of the present invention such as that disclosed in U.S. Pat. No. 3,954,102 to Buuck and U.S. Pat. No. 4,424,807 to Evans, Sr., and U.S. Pat. No. 5,263,981 to Polyak et al., herein incorporated by reference, basically comprises a prosthetic device 50 a pair of cylinders 51 and 54, a valve and pump assembly 58, a fluid reservoir 61, and intercommunicating flexible conduits 60. The entire device 50 is arranged to be surgically implanted in the body, with the two cylinders 51 and 54 being disposed within the penis, with the combination valve and pump assembly 58, disposed in either the abdominal cavity or in the scrotum and with the reservoir 61 disposed with the abdominal cavity.

In accordance with one embodiment of the invention each cylinder 51 and 54 has a cradle 65 located about 5 mm from the distal end of the cylinder. The cradle is designed so that the distal tip of the insertion tool fits into the cradle. Once in position at the distal segment, the surgeon may secure the distal tip of the glans penis by holding the tip of the penis and the tool, then disengaging the tool from the cradle and pulling back from the glans penis. This procedure provides a method of implanting a penile prosthesis into the distal end of the corpus cavernosum without the need for using needle and sutures and results in the elimination of punctures to the glans penis. In another embodiment, the cradle is made by a cap or fold that is attache dot the tip of the cylinder, said cap or fold made of a softer silicone material thereby enabling the fold to open when the tool is inserted and fold back or close when the tool is removed.

The cylinders 51 and 54 are arranged for surgical implantation in respective corpus cavernosum and are constructed to mechanically expand the corpora cavernosa until the fibrous tissue envelope becomes tense, thereby producing a functional erection without the necessity for the corpora cavernosa to be engorged with blood. The cylinders are readily deflatable to enable the penis to become flaccid when an erection is no longer sought.

Figure 9:
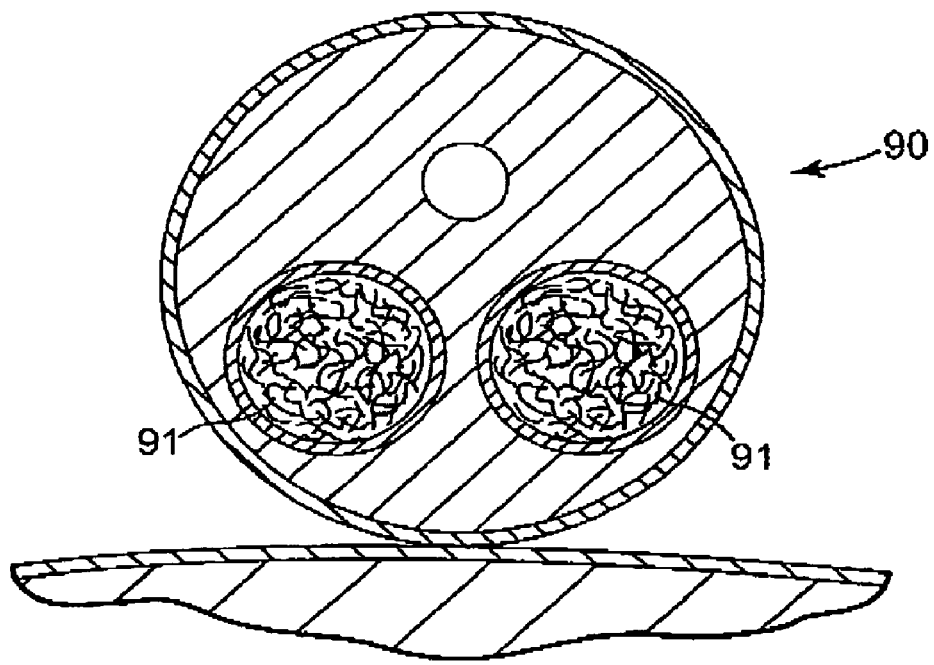
FIG. 9 is a sectional view of the glans penis.

The cylinders 51 and 54 are placed within the respective corpora cavernosum by surgically preparing a passageway 91 (FIG. 9) therein. The passageway 91 can be formed by any conventional surgical technique used for prior art penile implants. In FIG. 9, the passageways 91 are shown as being of circular cross-section. That shaped passageway is merely exemplary. Thus, it is to be understood that the passageways can be of any suitable shape. Each passageway 91 extends down a substantial portion of the length of the associated corporus cavernosum from a point adjacent the glans penis to a point adjacent the scrotum.

Each of the cylinders is an enclosed hollow member formed of a very thin, e.g., 2–5 mils, flexible membrane. As synthetic material, any appropriate material tolerated by the tissues may be used, and in particular silicone rubber. As can be seen clearly in FIG. 5, each cylinder is of generally cylindrical shape whose opposed ends are rounded or domed. The distal end of the cylinder is denoted by the reference numeral 52 and 55 and the proximal end by reference numerals 53 and 56. The distal end is arranged to be located adjacent the glans penis when the cylinder is located within the passageway and with the proximal end located adjacent the root of the penile shaft close to the scrotum. Each cylinder includes an opening or access port 62 to the interior thereof and which is located adjacent the proximal end of the cylinder.

The cylinders are arranged to be filled with a fluid, such as water, through its respective access port 62 to cause the cylinder to expand longitudinally, as well as radially. Since each cylinder is located in a respective passageway 91 in a corpora cavernosa, the expansion of the cylinder causes concomitant expansion of the corpora cavernosa from its minimal volume (its "flaccid volume") to an increased volume.

Each cylinder has sufficient volumetric capacity so that when it is inflated to the condition where the fibrous envelope surrounding the corpora cavernosa has reached the limit of its expansion, the material forming the membrane wall of the cylinder has not reached the point at which it undergoes tension, e.g., it does not begin to stretch.

The means for filling the cylinders 51 and 54 comprises the reservoir 61, the valve pump assembly 58 and the interconnecting tubing or conduits 60. To that end, the reservoir 61 is connected, via a tubing section, to one port 63 of the valve-pump assembly 58. The valve-pump assembly 58 comprises a squeezable bulb 59 coupled to interiorly located valves. The valve-pump assembly 58 also includes additional port(s) to which a conduit section is connected.

Operation of the device to produce an erection is as follows: The bulb 59 is squeezed through the skin of the scrotum, whereupon water from the reservoir 61 is forced through the port 63 and the tubing 64 to the associated access ports 62 of each of the cylinders. Thus, the cylinders begin to fill beyond the partially filled state. The pump bulb 59 has to be squeezed several times to effect a full erection. In this regard, each time that the pump bulb is squeezed, more water is forced into the cylinders through the conduit. Release of the pump or bulb 59 does not allow the water to return to the reservoir since the valve in the valve-pump assembly 58 is of the one-way type. Thus, each time the bulk is resqueezed, additional water is forced into the cylinders. This action causes the cylinders to expand from a flaccid condition to the fully filled or erect condition. In order to effect the filling of the cylinders, all that is required is pressure on the order of 21/2 psi. As long as the valve precludes the water in the cylinders from flowing back to the reservoir, the cylinders remain in their fully filled state and the erection is maintained. When it is desired to render the penis flaccid, all that is required is to actuate a release mechanism (not shown) forming a portion of the valve-pump assembly 58 by squeezing on the scrotum where the release mechanism is located, whereupon the valve in the assembly 58 enables the water to flow out of the cylinder and into the reservoir under the natural pressure caused by the resiliency of the fibrous envelope on the cylinders. When the pressure produced on the water in the cylinders by fibrous tissue envelope equals the pressure on the water in the reservoir, the flow of water ceases. Thus, the pump bulb 59 must be squeezed to force the water back into the reservoir so that the cylinders are back in their partially deflated condition, whereupon the penis is limp and flaccid.

Figure 8:
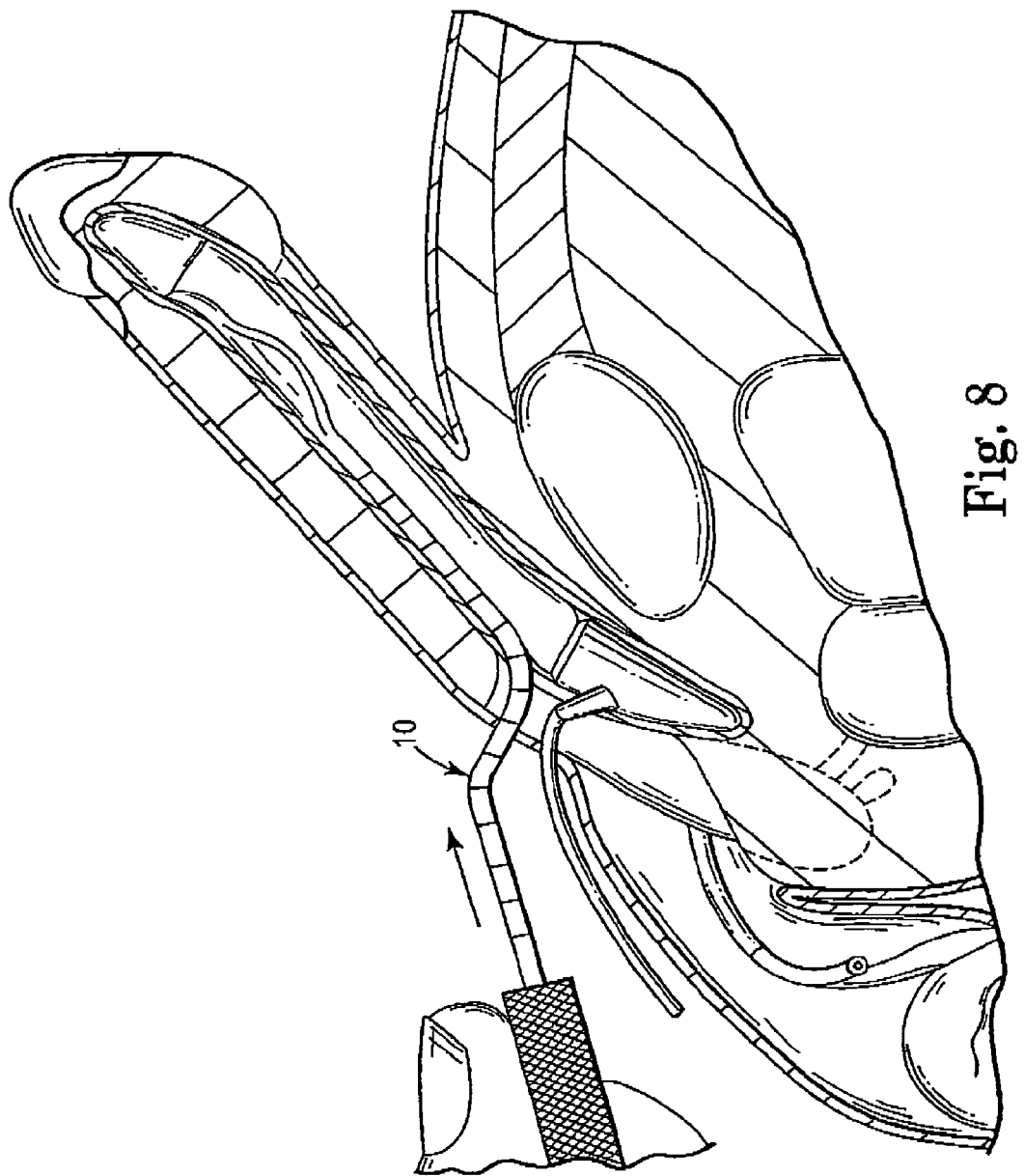
FIG. 8 illustrates the implantation of a cylinder containing a cradle on the distal tip of the cylinder together with the insertion tool.

The distal end of the improved penile prosthesis of the present invention may be inserted without the use of needle with the aid of the distal insertion tool of the present invention as illustrated in FIGS. 6, 7 and 8. The totally deflated cylinder of the present invention is inserted together with the tool into the corpora all the way into the distal most aspect of the penis to the level of the mid glans. At that point the tip of the prosthesis would be secured within the penis by the surgeon and the insertion tool and suture pulled back out of the penis.

The tools of the present invention may be made of any suitable materials for surgical instruments. In the illustrative embodiment shown, the tool of the present invention is an integral device made of stainless steel or plastic by known techniques, but can also be made of other materials. Tools made of plastics materials typically can be economically made to be disposable. The material and dimensions of the tools of the present invention are chosen so that the tools are substantially rigid, that is, does not bend significantly under normal operating conditions for which the tolls are intended, or provides sufficient columnar strength to advance the proximal cylinder end within the corporal body.

The tools of the present invention can also be partially or entirely coated with a layer of inert material that is compatible with both the penile prosthesis and human tissue, with both of which the tools is likely to contact. For example, silicone or parylene can be applied to the tools of the present invention to produce a smoother surface, reducing the chances of injuring either the implant or tissue. The coated surface may also be more compatible with the surrounding tissue, reducing the probability of adverse reactions by the tissue. If the handle portion of the tools of the present invention is also coated, the coating can provide a more secure grip by the surgeon's gloved hand. The coating can be applied by a variety of known techniques, including simply dipping at least a portion of the insertion tool of the present invention in a suspension of the coating material and overmolding. The uncoated surfaces of the tool can be deliberately roughened in preparation of coating to ensure superior bonding between the uncoated surfaces and the coating materials. Alternatively, one or more holes can be formed on the uncoated surfaces of the tool of the present invention so that dipped or overmolded material becomes mechanically attached to the tool by one or more anchors formed in the hole(s).

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A device for implanting the distal tip of a penile implant prosthesis without puncturing the glans penis, said device comprising an elongated body having a handle portion at one end, an intermediate portion, and a tip portion that includes a hole at the opposing end to secure a suture, wherein said intermediate portion includes an outwardly angled shaft section and linear handle section, and wherein the linear handle section is aligned in spaced and parallel relation to the axis of the outwardly angled shaft section, and wherein said outwardly angled shaft section has a convexity sized to accommodate and partially surround said distal tip of said penile implant prosthesis along a length of said distal tip.

2. The device according to claim 1, wherein said outwardly angled shaft section has a convexity ranging from about 0.5 cm to about 1.5 cm.

3. The device according to claim 1, wherein said outwardly angled shaft section of said intermediate portion has measurements calibrated to accommodate prosthesis dimensions and inform the operator of the exact distance of the distal tip inside the penile shaft.

4. An improved penile prosthesis device comprising;
  a. at least one cylinder having a proximal portion and a distal portion implantable within a corpus cavemosum of the penis, said cylinder having a defined, tool-engaging cradle on the external surface of a distal tip of the distal portion;
  b. a fluid containing reservoir;
  c. a pump chamber attached to said reservoir chamber;
  d. a means coupled to said cylinder and said pump chamber for providing fluid communication between said cylinder and said pump chamber; and
  e. a means for controlling fluid communication between said reservoir chamber and said pump chamber; wherein said cradle allows the insertion of the distal tip of said penile prosthesis to be implanted into the glans penis without puncturing said glans penis.

5. A penile prosthesis according to claim 4, which is made of silicone.

6. A penile prosthesis according to claim 4 wherein the cradle is made by a fold that is attached to the tip of the cylinder.

7. The penile prosthesis according to claim 4, wherein the cradle is located about 5 mm from the distal tip of the cylinder.

8. The cradle of claim 4, which is made of soft silicone.

9. A method of implanting the penile prosthesis of claim 4 without puncturing the glans penis or the penile prosthesis, said method comprising the steps of
  a. inserting a totally deflated cylinder together with an insertion tool though an aperture into the corpus cavernosum;

b. securing the distal tip by holding the tip of the penis and the tool;

c. disengaging the tool from the cradle; and e. pulling the tool back and out of the glans penis.

10. The method of claim 9 wherein said aperture is smaller than that required with an inflated cylinder.

11. The method of claim 9 wherein insertion of the deflated cylinder requires only a small aperture, resulting in a decrease in post-operative scarring.

12. The method of claim 9 wherein said insertion tool comprises an elongated shaft including a handle at one end and a blunt end at the opposite ends, and wherein said blunt end is designed to conform to the cradle in the prosthesis.

13. A method of implanting a penile prosthesis device without puncturing the glans penis or the penile prosthesis, said method comprising the steps of:

a. threading a suture through the opening located at the distal tip of an insertion tool having a shaft with an opening therein;

b. securing said suture around the shaft opening so as to fasten the cylinder of said penile prosthesis to the distal tip of said insertion tool;

c. positioning the distal tip of the prosthesis cylinder for implantation; and d. pulling the insertion tool and suture back out of the penis.

14. A method of implanting a penile prosthesis device, that includes a cylinder, without puncturing the glans penis or the penile prosthesis, said method comprising the steps of:

a. threading a suture through the opening located at the distal lip of an insertion tool;

b. securing said suture substantially about an external circumference of a distal end of said cylinder below a distal tip of said cylinder so as to secure the cylinder of said penile prosthesis to the distal tip of said insertion tool;

c. positioning the distal tip of the prosthesis cylinder for implantation; and d. pulling the insertion tool and suture back out of the penis.

* * * * *

UNITED STATES PATENT AND TRADEMARK OFFICE
CERTIFICATE OF CORRECTION

| | | |
|---|---|---|
| PATENT NO. | : 7,066,878 B2 | Page 1 of 1 |
| APPLICATION NO. | : 10/713437 | |
| DATED | : June 27, 2006 | |
| INVENTOR(S) | : J. Francois Eid | |

It is certified that error appears in the above-identified patent and that said Letters Patent is hereby corrected as shown below:

Column 2, line 57, "improve" should be -- improved --.

Column 6, line 21, "fro" should be -- for --; line 61, "fro" should be -- from --, line 65, "precisely" should be -- precise --.

Column 8, line 2, "attache dot" should be -- attaché dot --.

Column 9, line 11, "21/2" should be -- 2-1/2 -- ; line 46, "tolls" should be -- tools --.

Signed and Sealed this

First Day of May, 2007

JON W. DUDAS
*Director of the United States Patent and Trademark Office*